United States Patent [19]

Roque et al.

[11] Patent Number: 5,731,511
[45] Date of Patent: Mar. 24, 1998

[54] MEASURING CELL WITH MULTIPLE PRESSURE TAPS

[75] Inventors: Claude Roque, Chatou; Gerard Thibault, Colombes, both of France

[73] Assignee: Institut Francais du Petrole, Rueil Malmaison, France

[21] Appl. No.: 645,071

[22] Filed: May 13, 1996

[51] Int. Cl.⁶ .................................................. G01N 15/08
[52] U.S. Cl. .................................................................. 73/38
[58] Field of Search ............................... 73/38, 152.11, 73/152.09, 152.07

[56] References Cited

U.S. PATENT DOCUMENTS 2,345,935  4/1944  Hassler ............................. 73/38
2,821,680  1/1958  Slusser et al. .................... 73/38
4,848,145  7/1989  Blaschke et al. .............. 73/38 X
4,868,751  9/1989  Dogru et al. ................... 73/38 X
4,996,872  3/1991  Mueller et al. ..................... 73/38
5,086,643  2/1992  Marek ................................. 73/38

FOREIGN PATENT DOCUMENTS 2280512  2/1995  United Kingdom .

*Primary Examiner*—Michael Brock
*Attorney, Agent, or Firm*—Antonelli, Terry, Stout, & Kraus, LLP

[57] ABSTRACT

A device for studying the interaction of a fluid flowing in a porous medium surrounded by a membrane and subjected to a confining pressure includes on at least part of the circumferential periphery of the membrane, a groove connected to a pressure tap for measuring or detecting the pressure prevailing at the groove.

5 Claims, 3 Drawing Sheets

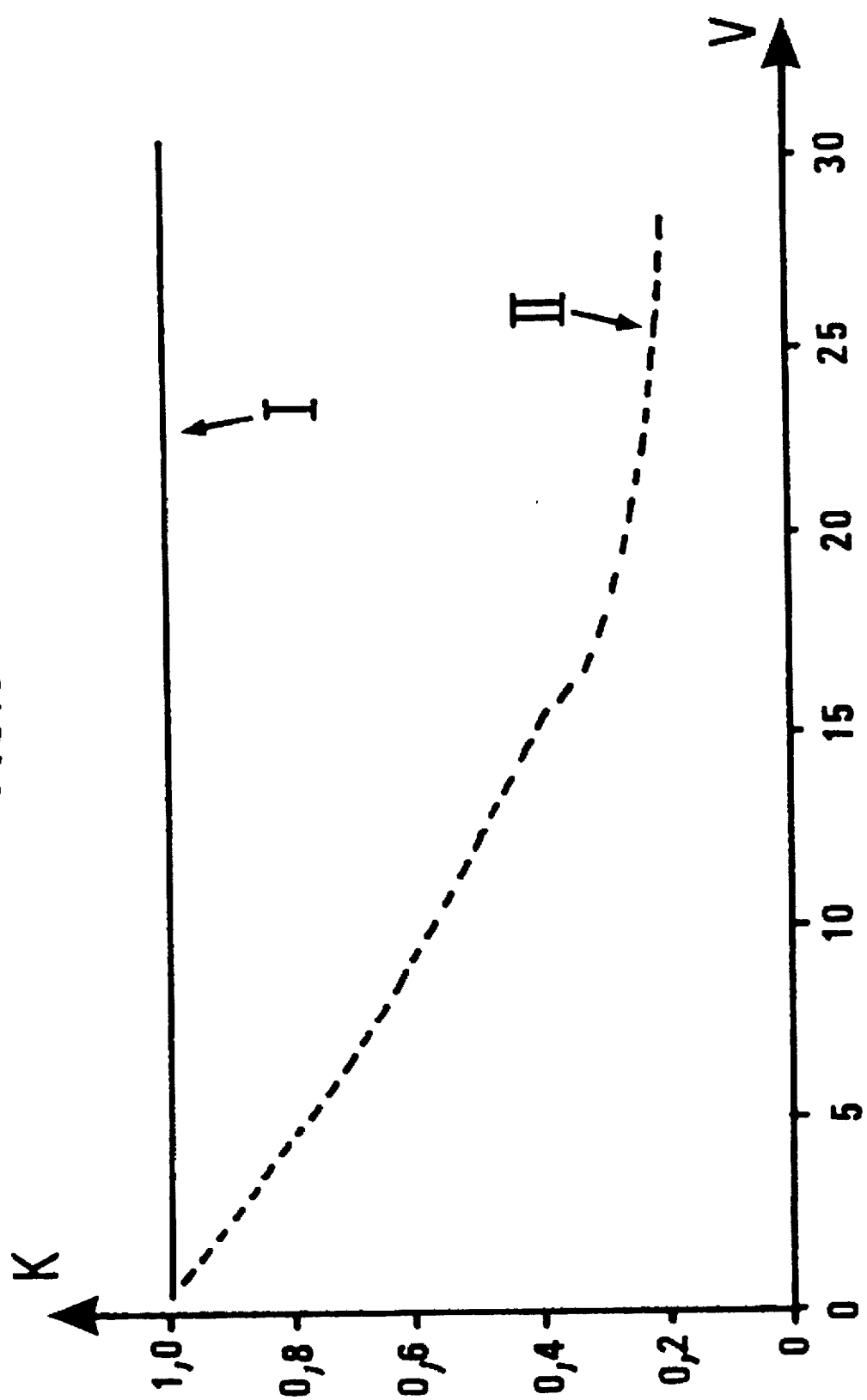

MEASURING CELL WITH MULTIPLE PRESSURE TAPS

FIELD OF THE INVENTION

The present invention relates to a device or Hassler type pressure measuring cell allowing notably to measure the interaction of a fluid circulating in a porous medium and the porous medium.

The present invention advantageously allows to obtain this information by reproducing pressure, temperature and confining conditions close to oil reservoirs for example.

The present invention is particularly well suited for determining the permeability of a porous medium, heterogeneous or not, that comes from a geologic formation. It can thus be advantageously used in the petroleum field for controlling and/or for quantifying fluid/medium interaction phenomena, such as porous medium damage, restoration, stimulation or simply drainage phenomena.

The device according to the invention is advantageously used as a laboratory device allowing dynamic evaluation of the behaviour of porous media such as reservoir rocks with respect to a fluid.

Such a qualitative and/or quantitative evaluation notably allows to predict the behaviour of porous media where fluids may circulate on a scale allowing the results to be directly extrapolated or scaled.

BACKGROUND OF THE INVENTION

Control of a porous medium where a fluid circulates is mainly based on the determination of the permeability thereof. This permeability measurement is linked with the pressure drop due to the circulation of the fluid in the porous medium, and this fluid can be inert with respect to the medium or interact therewith.

One of the devices that are most often used in the prior art is the Hassler type cell. The porous medium whose behaviour is sought when subjected to the circulation of a fluid, inert or interacting therewith, is placed in a chamber, subjected to a confining pressure by means of a membrane surrounding the sample. The fluid is injected at one end of the porous medium and the pressure drop or pressure difference between the two ends of the porous medium is measured. According to Darcy's law, known to the man skilled in the art, the pressure drop measurement is representative, for example, of the permeability of the porous medium with respect to the fluid injected, and/or of the aforementioned phenomena. However, the measurement obtained thereby is an overall measurement and it may in some cases prove inaccurate, especially for rocks exhibiting great local heterogeneities.

A first improvement consisted in positioning pressure taps or devices allowing to determine the pressure in different places situated along the length of a sample of a porous medium, in order to determine for example the permeability value of the porous medium for various sample sections or to study the fluid/porous medium interaction phenomena for various sections. The membrane surrounding the sample is therefore provided with several openings distributed along the sample and allowing access to the pressure existing at the level of a given section. However, such a point pressure measurement can still limit the accuracy of the pressure value since one wins access to a mean value of the pressure prevailing mainly in a zone situated in the neighbourhood of the opening. Such a measurement can thus hide certain heterogeneities distributed in the three dimensions of the porous medium.

The aforementioned devices and methods from the prior art offer limited information relative to various phenomena likely to occur when a fluid circulates in a porous medium, and they do not allow to obtain precise information on the total sample in space in three dimensions.

SUMMARY OF THE INVENTION

The present invention proposes a device that allows to overcome these drawbacks and notably to evaluate the interaction or effect of a fluid circulating in a porous medium with or on this medium, spatially in a three-dimensional volume of the sample. Such a measurement thus takes account of the heterogeneities that may exist in the porous medium.

To that effect, the invention proposes a device allowing to determine, spatially or in three dimensions, the interaction of a fluid circulating in a sample of a porous medium for a given section, by carrying out a pressure measurement by means of a groove situated at least on part of the periphery of a given section of the porous medium. Such a pressure measurement notably allows to have access to the value of the pressure prevailing in the entire section situated in the neighbourhood of the groove. Value of the pressure may be determined from a part at least of the fluid flowing through the sample and in particular the fluid passing at the level of the groove periphery and in the neighbourhood. Another possibility consists in filling the groove with a fluid, preferably inert with respect to the porous medium, that will allow indirectly to measure the pressure prevailing in the section of the porous medium. The circulating fluid can be inert or interactive with respect to the medium, and chosen in relation to the study of the mechanism of interaction.

Several grooves distributed along the length of the sample allow to increase advantageously the pressure measurement accuracy and therefore knowledge of the effects between a fluid and a porous medium.

Such a layout of the grooves on the membrane advantageously allows to reproduce the real conditions in which a porous medium can be.

The present invention relates to a device allowing to determine the interaction or the effect of a fluid circulating or flowing in a porous medium, with the porous medium, said porous medium being surrounded by a membrane and positioned in a chamber, said chamber being provided with at least one supply means delivering the fluid to be injected into the porous medium, situated at a first end of the chamber, and with at least one outlet pipe for the fluid that has flowed through the porous medium, the inner walls of the chamber and the outer face of the membrane thus creating a containment space.

It is characterized in that the inner wall of the membrane comprises, on at least part of the circumference thereof, at least one groove, the groove being connected to a means for determining the fluid pressure prevailing at the level of the groove, the means being inserted or embedded in the membrane.

According to an embodiment, the device according to the invention can comprise several grooves distributed along the membrane at distances selected with respect to the face of inflow of the fluid in the porous medium, as a function of the interaction studied between the fluid and the porous medium.

At least one of said grooves can extend over the total circumferential periphery of the membrane.

According to another embodiment, the membrane can include several grooves separate from each other, i.e. that do not communicate with each other, situated on the same periphery of the membrane and connected each to a means allowing the pressure to be detected.

The means allowing the pressure to be detected comprises, for example, an insert fitted in the membrane.

Each of the inserts can be connected to a tube such as a capillary containing a fluid such as a liquid, the capillary passing through the containment space before it runs through one of the ends of the chamber.

The device according to the invention is particularly well suited for measuring the permeability of a porous medium and/or for studying the kinetics of clogging of a porous medium by a fluid and/or for studying the damage to a porous medium resulting from the circulation of a fluid and/or for studying the interaction between a fluid circulating in a mother rock containing hydrocarbons.

The device according to the invention advantageously allows to evaluate quantitatively and/or qualitatively the interaction phenomena existing between a porous medium and a fluid circulating in the medium.

It can thus be used in order to:

evaluate the damage to porous media caused by a fluid containing particles and/or likely to interact physico-chemically with the medium so as to form particles that will circulate in the porous medium, study the restoration or the stimulation of a porous medium into which a solvent or an acid type fluid is injected, evaluate the drainage or enhanced recovery properties of a porous medium saturated by an oil and into which a fluid allowing oil circulation to be improved is injected, measure the permeability of a mother rock or reservoir rock sample.

It can also be used in all the fields where the behaviour of the pair formed by the porous medium and the fluid circulating therein is to be studied.

The sample on which the pressure measurements are performed is selected so as to be the most representative of the medium from which it is taken.

BRIEF DESCRIPTION OF THE DRAWINGS

Other features and advantages of the present invention will be clear from reading the description hereafter, given by way of non limitative examples, with reference to the accompanying drawings in which.

DESCRIPTION OF THE PREFERRED EMBODIMENTS

The principle used in the invention consists in performing measurements of the pressure of a fluid contained in a groove or slot, in several places, suitably selected according to the nature of the analysis to be carried out. The object of the analysis is notably to determine the interaction of a fluid circulating in a porous medium with this medium. The pressure prevailing at the level of a section of the porous medium is transmitted statically to a pressure measuring device.

Transmission of the pressure may be realized, for example, by using the fluid circulating in the porous medium, or using a fluid inert with respect to the porous medium and the fluid circulating, this fluid being initially placed inside the groove, as described below.

The pressure measurement is thus representative of the pressure coming from different places spatially distributed in the neighbourhood of the groove or groove portions concerned, therefore more representative of interaction phenomena that are usually evaluated by a point measurement.

In order to better define the principle of the device according to the invention, the description given hereafter by way of non limitative example is used to measure the permeability of a porous medium saturated by a fluid, coming for example from an oil reservoir exhibiting a certain degree of heterogeneity.

Figure 1:
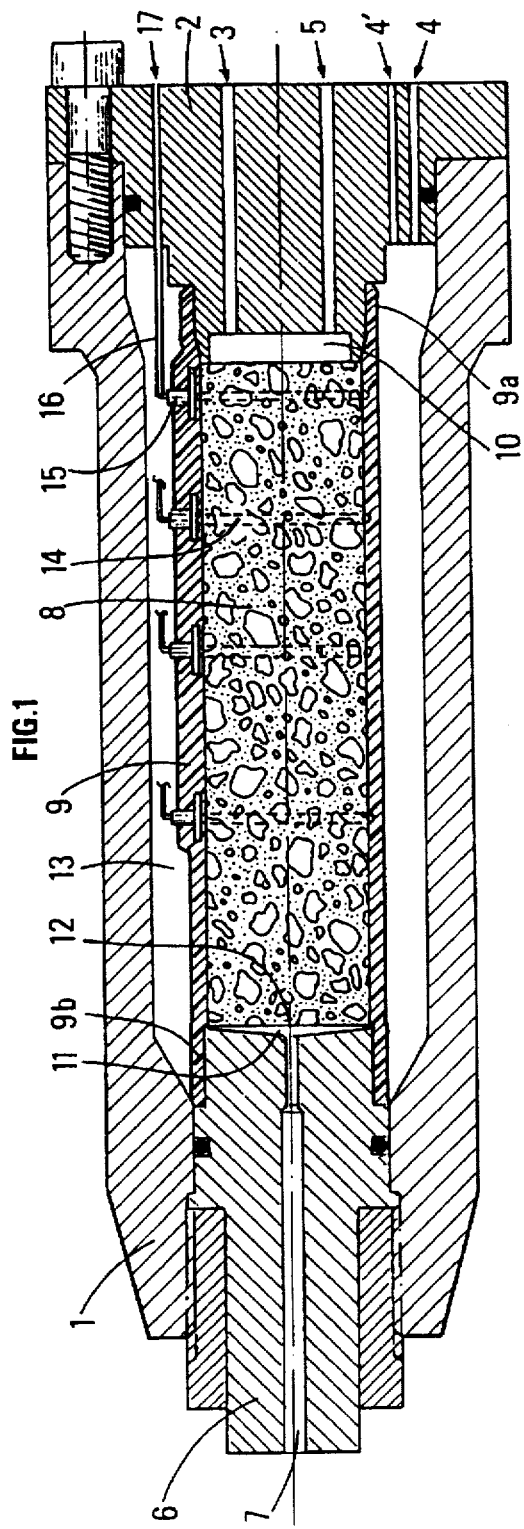
FIG. 1 illustrates the device according to the invention in its entirety.

The device described in FIG. 1 is a modified Hassler type cell in which a sample of the porous medium to be studied has been placed. The sample is for example a cylindrical core.

It comprises a chamber 1 closed at a first end thereof for example by a first part 2 comprising at least one supply pipe 3 delivering a fluid intended to be injected into the porous medium to be studied and that can be connected to an injection pump. The fluid is intended to circulate in the medium and to saturate it.

The first part or flushing head 2 also comprises a feed pipe 4 for delivering a confining fluid, that can be connected to a pump allowing to generate a confining fluid at a pressure value sufficient to prevent any leak at the sample surface and at the ends thereof, and a drain pipe 4' for discharging the confining fluid.

A drain pipe 5 for discharging the saturation fluid is for example positioned in the flushing head.

Chamber 1 is closed at a second end, for example situated at the end opposite the first part 2, by a second part 6 provided with at least one outlet pipe 7 intended for the fluid that has flowed through the porous medium.

The inner walls of chamber 1, of the first part 2 and of the second part 6 delimit the inside of the measuring cell where the sample is placed.

The sample 8 to be analyzed is surrounded by a membrane 9 and positioned inside chamber 1 between respectively the first part 2 and the second part 6. Membrane 9 is for example cylindrical and it surrounds the sample over at least the total length thereof and it preferably extends beyond it so as to rest on the first and second parts and to provide thereby a seal for the assembly by bringing pressure to bear on it, i.e. on the inlet side between flushing head 2, the space 10 situated before the sample and the sample, and on the outlet side of the cell, between the sample and the outlet part. Membrane 9 thus surrounds the flushing head over a length 9a and the outlet part over a length 9b.

Such an embodiment allows to provide a complete seal for the assembly.

Preferentially, membrane is realized in an enough supple material in order to assure tightness contact with the porous medium. Material such as Adiprene® (a polyurethane rubber) or Vitron® (a fluorinated elastomer) may be employed.

The porous medium sample 8 is placed for example at a given distance from the first part so as to create a space 10 of delivery of the fluid intended to be injected into the porous medium. The volume of delivery space 10 can be adjustable and it is selected notably as a function of the nature and of the amount of fluid injected into the porous medium. It also allows the fluid injected to be preferably uniformly distributed with respect to the inlet face of the porous sample and to sweep substantially the total surface thereof. What is understood to be the inlet face of the porous sample is the face that receives the fluid injected and therefore the face positioned near to the flushing head.

This is true whatever the way the fluid is injected, in a matrical, tangential manner or under mechanical agitation; in the latter case, an agitator known to the man skilled in the art, placed at the level of space 10, can be used.

The sample saturation fluid flows out of pipe 3, passes through space 10 prior to penetrating the sample, for example in a matrical way.

The saturation fluid penetrates and infiltrates into the porous sample prior to flowing out mainly through outlet pipe 7. When the grooves are not initially filled with inert fluid, one part of the fluid circulating in porous sample fills the grooves situated in the membrane. This part of fluid allows the measurement of the pression to be realized.

The end 11 of the second part situated opposite the sample advantageously has a shape suited to create a space 12 whose conical shape for example drains the fluid that has flowed through the sample and discharges it through the fluid outlet pipe 7 with which it communicates.

The inner walls of chamber 1, of the first part and of the second part delimit a space 13 with the sample. Thus, for the device of FIG. 1, the inside diameter of the chamber and the outside diameter of sample 8 surrounded by membrane 9 are selected to create an annular space 13 filled for example with a pressurized confining fluid flowing in through pipe 4 in order to create a confining pressure around the sample. The pressure presses the membrane on the sample and on the end parts of the cell. The confining fluid is placed under pressure by means of a device such as a pump, not shown in the figure for simplification reasons, connected to the pipe delivering the confining fluid.

The confining fluid around the membrane thus advantageously allows to reproduce the confining pressure or natural geostatic pressure under which the analyzed rock is placed.

The inner wall 9' of the cylindrical membrane 9 adjusted to the diameter of the sample comprises, for example, several grooves 14 extending over the total circumference thereof. Each groove 14 is connected to a pressure tap consisting for example of an insert 15 embedded in membrane 9. A insert is for example connected to a tube 16 filled with a fluid such as a liquid transmitting information and communicating with devices that are commonly used, for example valves, pressure detectors and means for processing the information obtained, not shown in the figure for clarity reasons.

Figure 2B:
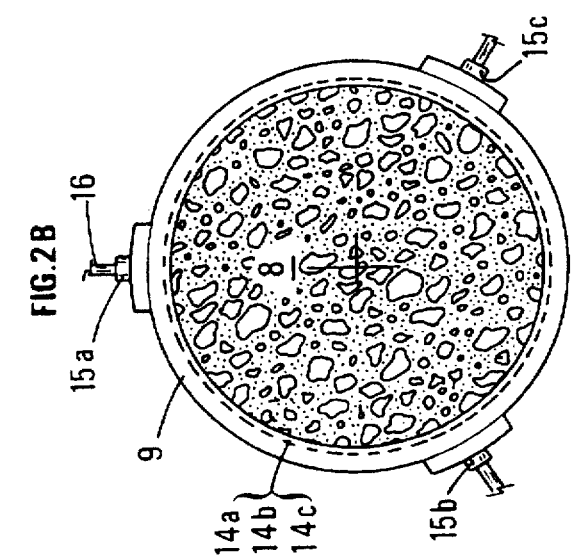
FIGS. 2A and 2B show a detailed embodiment example of a membrane comprising several grooves extending over the total circumference thereof, the curves of FIGS. 3A and 3B are application examples of the invention for studying the kinetics of damage phenomena due to the circulation of a fluid containing particles, and FIG. 4 diagrammatically shows another embodiment according to the invention where the membrane is provided with several groove sections distributed on the same circumference.
Figure 2A:
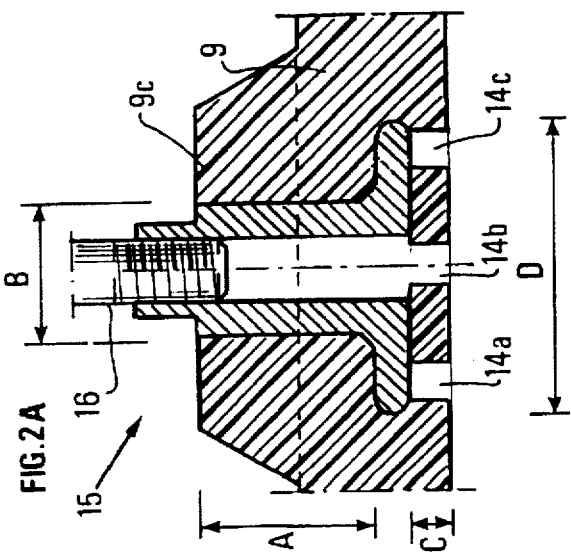

One embodiment variant for the positionnement and the shape of the insert 15, preferably, metallic insert, inside the supple membrane is shown on FIG. 2A.

Insert 15 allowing the pressure tap through the membrane may be described with the following characteristics parameters or sizes referenced:

A=height of the cylindrical part of the insert,
B=diameter of the shank used to take the pressure,
C=thickness of the supple membrane comprised between the base of the insert and the part of the membrane in contact with the porous medium,
D=diameter of the base of the insert.

To assure a good rapidity of the pressure tap, the insert must be preferably embedded inside the elastic or supple material of the membrane, or example simultaneously of the manufacture of the membrane (pouring of the material of the membrane) and preferably the parameters must be such as:

$A \geq B$
$C \geq 1$ mm, and
D such as $3B > D > 2B$.

Moreover, the membrane 9 preferably has an excess thickness 9c. This excess thickness 9c is placed relative to each insert 15, and the whole thickness of the membrane 9 and the excess thickness, completely cover the height A of the cylindrical part, as shown in FIG. 2A.

Preferably, the geometry and sizes of the insert have no sharp angles in order to avoid the problem of local tearing of the membrane when subjected to stress.

Figure 4:
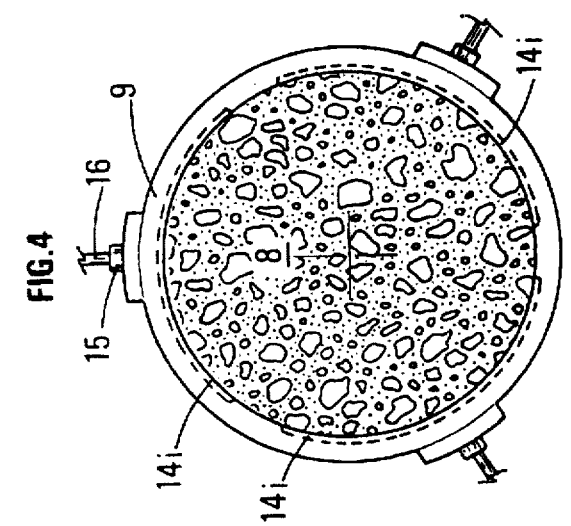

Embodiment variants for the shapes of grooves 14 are given in detail in FIGS. 2A, 2B and 4 described hereafter.

It is possible to realize pressure tap measurements in different ways. One possible way consists in using the fluid circulating through the porous medium, and a second possible way consists in using an inert fluid initially placed in the grooves. Transmission between the fluid filling the groove and the liquid inside the capillary 16 allows the measurement of pressure. Filling of the grooves may occur, for example, through the capillary 16 and the insert 15.

In first case, under the effect of the confining pressure, part of the fluid contained in the sample fills each of the grooves situated around one or more given sections of the sample. All of the fluid filling a groove is thus spatially representative of the pressure existing at the level of the sample section situated opposite the groove and close to the section, and reflects the interaction phenomena that occurred between the fluid circulating in the porous medium and the porous medium.

The pressure is transmitted statically by means of the fluid present in capillary 16 up to a measuring device such as a pressure detector, not shown in the figure.

An array of valves connected each to a capillary 16 allows for example advantageously to select the grooves for which measurements are achieved.

All these devices are for example connected to a control and data processing device, for example a microcomputer. The latter can also manage the feeding, in a quantitative, qualitative and temporal manner, of the fluid injected into the porous medium.

It can also control the drain pipes for discharging the confining fluid and the fluid injected into the sample.

According to the second mode of implementation of the method, the grooves are initially filled with a fluid inert with respect to the porous medium and the fluid circulating through the porous medium. In this case, the pressure prevailing at the level of a sample section is transmitted and determined by means of the inert fluid. The filling of the groove may be realized through the capillary 16 and the insert 15.

The tubes or capillaries 16 advantageously run through the annular space 13 before they run out of the device through suitable openings 17 provided in the flushing head. Such a layout allows to decrease the overall dimensions of the device.

The nature of the fluid circulating in the porous medium, or sweep fluid, is selected as a function of the analysis conducted, various examples are given in the description hereafter.

The injected fluid can thus interact chemically with the porous medium, for example by dissolving part of the medium, physically and/or have physico-chemical chemical effects with the porous medium in which it circulates. It can also be inert with respect to the medium.

Such a device is advantageously used to determine the permeability of a reservoir sample for a given fluid.

The sample to be studied is positioned in the cell as described above.

The sweep fluid introduced under pressure through supply pipe 3 is delivered in space 10 in which it is distributed so as to sweep the total surface of the sample and to infiltrate into it. The fluid is preferably introduced in sufficient amount in order to saturate the sample. The amount of sweep fluid fed into space 10 can be controlled by means of a valve connected to the injection pipe, and this valve can be operated by manual control or by the microcomputer. A confining fluid is injected for example simultaneously into the annular space 13 so as to generate the confining pressure or to reproduce a geostatic pressure around the sample to be tested.

For grooves that were not initially filled, at least part of the fluid circulating in the porous medium and subjected to the confining pressure flows into grooves 14 or the groove sections present in the inner wall of membrane 9.

Insert 15, respectively connected to a groove 14 and to a capillary 16, transmits, by means of the liquid contained in the capillary, a signal representative of the pressure prevailing in a given sample section or portion of the porous sample situated close to the groove or groove sections.

In the example described in FIGS. 2A and 2B, the sample is a cylindrical core and the inner wall of membrane 9 comprises for example three slots or grooves 14a, 14b, 14c distributed along the length of the membrane, for example over a length of 1 cm. Such a layout is particularly suitable when one intends to study interactions between the fluid and the rock or the sample, which occur at a short interval from the fluid inflow face, near to or in the neighbourhood of the latter. For reasons of space, the inserts 15a, 15b, 15c connected to grooves 14a, 14b, 14c are offset with respect to each other for example at an angle of 120° (FIG. 2B). The amount of fluid on which the pressure is measured at the level of an insert connected to a groove is greater than that which is available in the case of a point measurement. In fact, the volume of the groove collecting the fluid corresponds substantially to the total surface of the periphery of the sample section considered, as well as to the neighbourhood thereof.

The measurement accuracy is thus increased in relation to point measurements.

This reasoning remains true when the grooves are initially filled with a fluid inert with respect to the porous medium, that acts as a means of transmission of the pressure prevailing at the level of a section of the medium up to the measurement detector.

For example, for the device described in FIG. 1, that comprises 6 grooves situated respectively at distances $x_1, x_2, x_3, \ldots x_6$ from the sample inlet face for example, the information obtained at the level of each of the pressure taps is transmitted by means of capillaries 16 to the pressure detectors placed outside the device and then to the data processing device.

Interpretation of the signals is achieved according to a principle that is commonly used by the man skilled in the subject applying Darcy's law and it notably allows to obtain the permeability values of the porous medium for various sections.

The nature of the fluid injected into the porous medium or sweep fluid studied is selected as a function of the desired analysis.

In some cases, it is advantageous to use a fluid that is inert with respect to the porous medium, which will allow to obtain an image of the heterogeneity of the sample for a set of partial measurements of the permeability allowing to obtain a permeability profile.

When the damage caused to a porous medium by a fluid is to be studied, it is possible to feed a fluid that will interact with the porous medium, cause a certain dissolving of the medium and a certain crystallization in some cases. The dissolving and/or crystallization phenomena will then lead to the clogging of the pores of the medium with different degrees of clogging according to places, spatially distributed around a given section or with respect to the distance from the inlet face of the medium, i.e. the face receiving the fluid.

The layout of several grooves or groove sections distributed along the sample allows to achieve a pressure drop profile for several positions and thus to know, by applying Darcy's law, the sensitivity of the various zones concerned.

For rock restoration studies, an acid type fluid is for example injected into the medium. This fluid has notably the effect of changing the porosity of the porous medium.

By means of the pressure measurements described above, the depth of action of the acid in the porous medium can be studied. In fact, the shape of the pressure difference or pressure drop curve for a given section situated at a distance x from the fluid inflow face allows to know quantitatively and/or qualitatively the effect of an acid injected into a porous medium that can be a sample taken from a reservoir rock. Such response curves are applicable to studies relative to the stimulation of reservoirs by means of acid type fluids and they are usually referred to as acid response curves.

They optionally allow to evaluate, quantitatively and/or qualitatively, obstructed zones due for example to the particles detached from the porous medium under the action of the acid on the porous medium.

These results can be coupled with physico-chemical analyses of the fluid that has flowed through the porous medium, allowing to fine down the understanding of interaction phenomena that occurred while the fluid passed through the porous medium.

Another possibility consists in studying the drainage of a porous medium. The porous medium being filled with a fluid such as oil in the case of a reservoir rock sample, a mixture consisting of water and a polymer is for example injected and the pressure drop values are measured in different places along the sample.

The device can be positioned in a medium whose temperature and pressure conditions are controlled.

The number and the position of the grooves along the membrane are selected as a function of the porous medium studied and of the fluid injected into this medium.

In fact, the fluid injected into the porous medium to be studied interacts or not with the latter according to its nature, and in different ways throughout its progress through the sample.

Figure 3B:
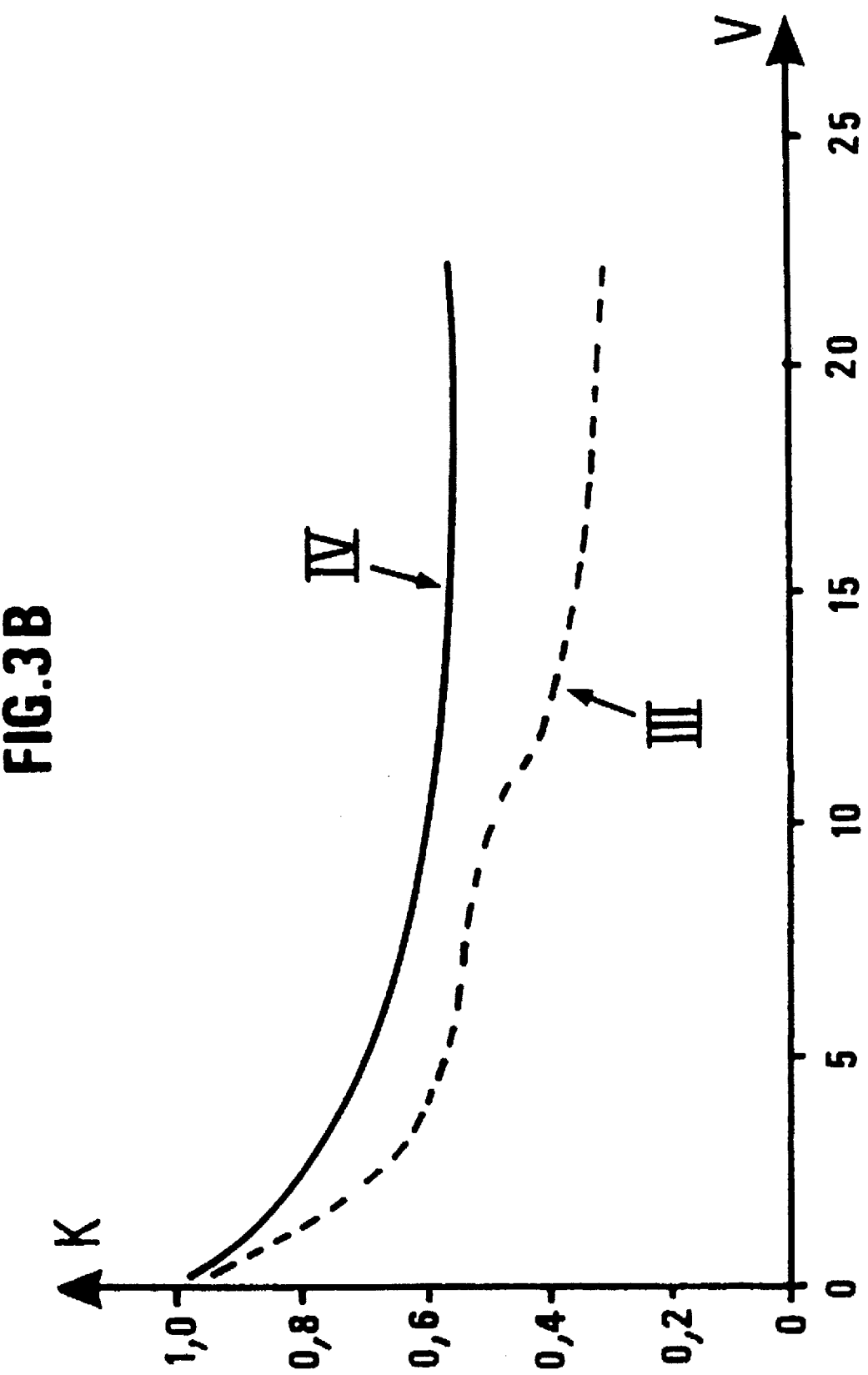

FIGS. 3A and 3B show examples where the device according to the invention is applied to the study of the kinetics of clogging of a porous sample while a fluid circulates therein.

Curves 3A and 3B represent evolution curves of the permeability values obtained by dynamic measurement, showing the kinetics and the depth of clogging of a porous medium by a fluid containing particles, injected into the medium as a function of the cumulative volume of fluid injected and under conditions indicated in Table I hereafter. The permeability values were obtained from values relative to the pressure drop or pressure difference existing between a measuring point situated at the level of a groove and the inlet face of the sample by applying Darcy's law.

TABLE I

Porous medium clogging test by particle injection

| Exper. | U cm/min | Qv mL/min | Dp μm | Ci mg/L | Kwi mD | Ø % | l mm |
|---|---|---|---|---|---|---|---|
| FIG. 3A | 1 | 3.0 | 7.6 | 14 | 1000 | 15.5 | 185 |
| FIG. 3B | 10 | 30 | 4.28 | 8 | 1075 | 16.1 | 99 |

U = interstitial velocity of the fluid in the porous medium,
Qv = flow rate of fluid injected into the porous sample analyzed,
Dp = diameter of the particles injected into the porous medium,
Ci = concentration of the particles injected into the porous medium,
Kwi = expressed in milliDarcy, initial permeability of the porous medium,
Ø = porosity of the porous medium,
l = length of the sample.

FIG. 3A shows a family of curves Kw/Kwi (Kw permeability of the porous medium and Kwi initial permeability of the porous medium measured by usual means, denoted by K in the figure for clarity reasons) showing the evolution of the ratio of the kinetics of clogging of the medium by the circulating fluid to the depth of clogging.

Curve I shows the evolution of the permeability of a porous medium with respect to the face of inflow of the fluid in the sample, as a function of the amount of fluid V injected. The fast variation of the slope of curve I reflects the case of a clogging by formation of a cake that forms slowly in the first millimeters of the sample. An average loss of about 70% can be noted for the permeability value of the sample, that is mainly due to the clogging of this first zone of the sample.

The points measured for sample sections situated at distances of respectively 7, 14, 36, 56, 78 mm from the inlet face correspond to a single line (II) that shows a non-variation of the permeability.

FIG. 3B, obtained under conditions given in Table I above, shows a curve (III) representative of the permeability variation of the porous medium in a first 0–2 mm-section of the fluid inflow face, which also shows a permeability decrease indicating the formation of a cake at the sample inlet and, furthermore, a curve (IV) that represents a permeability value of the more internal zones of the sample that is also affected by a so-called internal clogging.

Curve (III) is representative of the formation of a clogging at the level of the sample inlet through the formation of an external cake. The permeability of the porous medium reaches substantially a constant value that governs the whole sample.

The curves obtained by means of measuring points situated at distances of respectively 7, 14, 36, 56 and 78 mm from the inlet face are grouped together in the same curve (IV). The shape of curve (IV) reflects a permeability variation representative of a deep clogging of the sample.

FIG. 4 shows another embodiment variant where grooves 14 consist of several sections 14i distributed on a single circumference of a groove. Each of the groove sections is connected to a pressure tap 15 that allows to obtain information for a given sample section and for a given zone.

This procedure allows to fine down permeability measurements that may be different in a single sample section in the case of a porous medium exhibiting great heterogeneities, and notably to study spatially the distribution of the heterogeneities of a porous medium (in volume and in three dimensions).

We claim:

1. A device for determining the interaction or the effect of a fluid circulating or flowing in a porous medium, said porous medium being surrounded by a membrane and positioned in a chamber, said chamber being provided with at least one supply means delivering a fluid to be injected into the porous medium, situated at a first end of the chamber, and with at least one outlet pipe for discharging the fluid that has flowed through the porous medium, the inner walls of the chamber and the outer face of the membrane creating a containment space, wherein an inner wall of said membrane has at least one groove formed therein and arranged to extend on at least a part of the circumferential periphery of the membrane, said groove being connected to a means for detecting the fluid pressure prevailing at the groove, said means being inserted or embedded in said membrane, wherein the membrane has several grooves that do not communicate with each other, that are situated on the same circumferential periphery of the membrane, and that are connected each to a means for detecting the pressure.

2. A device as claimed in claim 1, wherein said means for detecting the pressure comprises an insert fitted in the membrane.

3. A device as claimed in claim 2, wherein the insert is a metallic element having a tubular portion which extends through at least part of the inner wall of said membrane, and said membrane comprises an elastic or supple material.

4. A device as claimed in claim 3, wherein said membrane comprises a tubular sleeve having a cylindrical portion which surrounds the porous medium and open end portions which surround and engage parts forming end portions of the chamber, said at least one supply means extending through one end part and the at least one outlet pipe extending through another end part.

5. A device for determining the interaction or the effect of a fluid circulating or flowing in a porous medium, said porous medium being surrounded by a membrane and positioned in a chamber, said chamber being provided with at least one supply means delivering a fluid to be injected into the porous medium, situated at a first end of the chamber, and with at least one outlet pipe for discharging the fluid that has flowed through the porous medium, the inner walls of the chamber and the outer face of the membrane creating a containment space, wherein an inner wall of said membrane has at least one groove formed therein and arranged to extend on at least a part of the circumferential periphery of the membrane, said groove being connected to a means for detecting the fluid pressure prevailing at the groove, said means being inserted or embedded in said membrane and comprising an insert fitted in the membrane and wherein each of the inserts is connected to a capillary tube containing a fluid, said capillary tube running through the containment space before the tube runs through one of the ends of the chamber.

* * * * *

UNITED STATES PATENT AND TRADEMARK OFFICE
CERTIFICATE OF CORRECTION

PATENT NO. : 5,731,511
DATED : March 24, 1998
INVENTOR(S) : Clalude Roque, et al.

It is certified that error appears in the above-identified patent and that said Letters Patent is hereby corrected as shown below:

On the title page, please add item [30] Priority:

Foreign Application Priority Data

May. 12, 1995 [FR] French.............................95 05894

Signed and Sealed this

Sixteenth Day of February, 1999

Attest:

Attesting Officer

*Acting Commissioner of Patents and Trademarks*